United States Patent [19]
Lindgren et al.

[11] Patent Number: 5,281,418
[45] Date of Patent: Jan. 25, 1994

[54] METHOD AND COMPOSITION FOR CONTROLLING MOUNTAIN PINE BEETLES

[75] Inventors: Bo S. Lindgren, Port Coquitlam; John H. Borden, Burnaby; Marek Gnatowski, New Westminister; Po C. Wong, Burnaby, all of Canada; Mark D. McGregor, deceased, late of Missoula, Mont., by Janice J. McGregor, executrix

[73] Assignee: Phero Tech Inc., Delta, Canada

[21] Appl. No.: 832,674

[22] Filed: Feb. 6, 1992

Related U.S. Application Data

[63] Continuation of Ser. No. 584,284, Sep. 18, 1990, abandoned.

[30] Foreign Application Priority Data

Sep. 22, 1989 [CA] Canada .................................. 612680

[51] Int. Cl.⁵ ...................... A01N 25/08; A01N 31/06
[52] U.S. Cl. ................................... 424/405; 424/408; 424/501; 424/84; 514/919
[58] Field of Search ............... 424/405, 406, 408, 410, 424/84, 405; 514/919

[56] References Cited

U.S. PATENT DOCUMENTS

| | | | |
|---|---|---|---|
| 4,170,631 | 10/1979 | Young et al. | 424/405 |
| 4,839,383 | 6/1989 | Vité | 424/405 X |
| 4,994,268 | 2/1991 | Wieser et al. | 424/84 |

OTHER PUBLICATIONS

Ryker, L. C. and K. L. Yandell. 1983. Effect of verbenone on aggregation of *Dendroctonus ponderosae* Hopkins (Coleoptera: Scolytidae) to synthetic Attractant. Z. Angew. Entomol. 96: 452–459.

David L. Wood. et al. 1976. Western pine beetle: specificity among enantiomers of male and female components of an attractant pheromone. Science. 192: 896–898.

Furniss, M. M., et al. 1981. Effectiveness of Douglas-fir anti-aggregative pheromone applied by helicopter. USDA For. Serv. Gen. Techn. Rep. Int-101, 6 pp., Intermountain For. and Range Exp. Stn., Ogden, Utah.

Furniss, M. M., et al. 1982. Aerial application of Douglas-fir beetle anti-aggregative pheromone; Equipment and evaluation. USDA For. Serv. Gen. Techn. Rep. INT-137, 9 pp., Intermountain For. and Range Exp. Stn., Ogden, Utah.

*Primary Examiner*—Thurman K. Page
*Assistant Examiner*—Neil Levy
*Attorney, Agent, or Firm*—Griffin, Butler, Whisenhunt & Kurtossy

[57] ABSTRACT

This invention relates to methods and compositions for combating mountain pine beetle (*Dendroctonus ponderosae*) which causes severe damage to pine trees in North America. A method and apparatus for reducing attack by mountain pine beetles *Dendroctonus ponderosae* on pine trees, Pinus species, by spacially deploying verbenone (4,6,6-trimethylbicyclo[3.1.1]hept-3-en-2-one) in stands of pine trees.

11 Claims, 1 Drawing Sheet

METHOD AND COMPOSITION FOR CONTROLLING MOUNTAIN PINE BEETLES

This is a continuation of application Ser. No. 07/584,284 filed Sep. 18, 1990, now abandoned.

FIELD OF THE INVENTION

This invention relates to methods and compositions for combating mountain pine beetle (*Dendroctonus ponderosae*) which causes severe damage to pine trees in North America.

BACKGROUND OF THE INVENTION

Several methods exist for management of mountain beetle population but few effectively prevent damage of high value pine trees, for example, in campgrounds near administrative sites, near summer homes and wildlife refuges, and in riparian zones. One method of management of the mountain pine beetle is to harvest infested trees and kill the beetles resident in the inner bark during milling. This method often fails because it is not feasible or desirable to harvest the pine trees before the beetles emerge and disperse to new trees; also, many stands of trees are inacceptible and harvesting of all infested or high risk stands is not compatible with management of other resource values.

Use of conventional chemical pesticides against the beetles is also of limited utility because the beetles spend most of their life protected under the bark of infested trees and thus do not come in lethal contact with the pesticides.

A new method of management of beetles is the use of semiochemicals (message-bearing chemicals). The mountain pine beetle produces and releases several attractive semiochemicals during tree colonization. Several of these chemicals are attractive to other beetles and serve to initiate mass attack on host trees (Borden et al. 1987). During initial and mass attack, the host tree releases extraordinarily high quantities of pitch which contain terpenes, some of which are attractive to the beetles. One of these terpenes, myrcene (7-methyl-3-methylene-1,6-octadiene) synergizes attraction of beetles to two beetle-produced attractants trans-verbenol (trans-4,6,6-trimethylbicyclo[3.1.1]hept-3-en-2-ol) and exo-brevicomin (exo-7-ethyl-5-methyl-6,8-dioxabicyclo-[3.2.1]octane) (Borden et al. 1983, 1986, 1987; Conn et al. 1983). A beetle attractive mixture of myrcene, trans-verbenol and exo-brevicomin is currently used in North America to bait trees on which it is desired to induce attack (Borden et al. 1986).

There are several current strategies for combatting the mountain pine beetle using these attractive semiochemicals. One involves attraction to baited trees within an infested area, to effect containment and concentration of the infestation prior to removal of the beetles by logging. A second involves attraction to baited trees in which the beetles will be killed by injection of a chemical pesticide, or treating the outside bark with lethal pesticides.

In some instances it is more desirable to repel the beetles from trees or stands by use of a repellant than it is to lure beetles to trees for the purpose of destroying both the tree and attracted beetles. This approach has been investigated using pine oil obtained from the pulping process but due to the high cost of experiment and registration, and possibly for its limited use in high value oils, further testing is not recommended at this time.

The negative enantiomer of verbenone (4,6,6-trimethylbicyclo[3.1.1]hept-3-en-2-one) has been shown to inhibit response of both sexes of the mountain pine beetle to the attractive volatiles, a-pinene, trans-verbenol and myrcene in laboratory bioassays, as well as in field trap bioassays (Ryker and Yandell, 1983). Verbenone has been shown to inhibit male beetle response to multiple funnel traps baited with attractive mixtures of trans-verbenol, exo-brevicomin and myrcene but it did not significantly alter response of female beetles to these baited traps (Borden et al. 1987). Vité (U.S. Pat. No. 4,839,383) discloses antiaggregant activity for the negative enantiomers of verbenone, endo-brevicomin and exo-brevicomin, on the southern pine beetle, *Dendroctonus frontalis*. His data cannot be extrapolated to other species of the genus Dendroctonus. Species within a genus may respond differently to the same compound, or its enantiomers. For example, the ambrosia beetle *Gnathotrichus sulcatus* is attracted by racemic sulcatol (6-methyl-5-hepten-2-ol), while *G. retusus*, a sympatric species, is attracted by S-(+)-sulcatol, while even as little as 5% of the R-(−)-enantiomer affects its response negatively (Borden et al. 1980). Lanier and Wood (1975) demonstrated that interspecific attraction to pheromones occurs mainly within the same species group in the genus Ips. They also demonstrated differences in attraction between two subspecies of *I. calligraphus*, and between eastern and western populations of *I. pini*. This shows that extrapolations of data from one species to another cannot always be made.

Several instances of repulsion of bark beetles by their own attractive chemical emissions have been documented. On the basis of trapping experiments, exo-brevicomin and endo-brevicomin (endo-7-ethyl-5-methyl-6,8-dioxabicyclo[3.2.1]octane have both been reported to exhibit repellant behaviour toward mountain pine beetle (Rudinsky et al. 1974a), yet exo-brevicomin is part of the presently used operational attractive bait used to lure these insects to baited trees. Frontalin (1,6-dimethyl-6,8-dioxabicyclo[3.2.1]octane) is produced by feeding male beetles and is reported to have a repellant effect in beetle trapping experiments (Libbey et al. 1985). However, frontalin has also been shown to induce attack on pine by the mountain pine beetle (Chatelain and Schenk, 1984) and has been shown to be attractive in one of two trapping experiments by Borden et al. (1987). Conversely, E-myrcenol has been shown to repel another bark beetle, *Ips pini*, from traps, but to induce attack on host logs (D. R. Miller, Unpublished).

3-Methyl-2-cyclo-hexen-1-one (MCH) has been shown to serve as an anti-aggregation pheromone for the Douglas-fir beetle, *Dendroctonus pseudotsugae*, and the spruce beetle, *D. rufipennis* (Rudinsky et al 1974b). An aerially applied bead formulation of MCH for protecting felled Douglas-fir trees (Furniss et al. 1981, 1982; McGregor et al. 1984) has been protected in U.S. Pat. No. 4,170,631 (Young, R. W. and M. M. Furniss, Oct. 9, 1979). The use of MCH formulated in bubble gaps and applied to the trunk of individual, felled Douglas-fir trees and spruce trees were demonstrated to be efficient for protection against attacks by Douglas-fir beetle and spruce beetle, respectively (Lindgren et al. 1988; 1989). Based on this knowledge, it is not possible to predict or infer the response of the mountain pine beetle to pine trees or pine forests treated with verbenone.

SUMMARY OF THE INVENTION

The invention pertains to methods and compositions for reducing attack by mountain pine beetles *Dendroctonus ponderosae* on pine trees, Pinus species, by placing verbenone (4,6,6-trimethylbicyclo[3.1.1]hept-3-en-2-one) in stands of pine for which it is desired to reduce attack. The verbenone may have 70-90% of its negative enantiomer. The verbenone may specifically have 83% of its negative enantiomer. In one aspect, method of reducing the attack rate of mountain pine beetles on pine trees in moderately infested stands comprises placing verbenone on some trees in the stand to reduce attack on these trees and the trees surrounding them. In another embodiment, the method of preventing attack by mountain pine beetles on pine trees in moderately-infested and uninfested stands of the pine trees involves placing verbenone on uninfested trees to prevent attack or of moving infestations of mountain pine beetle from infested stands of pine trees by placing verbenone on trees in the infested stands. In the method, the beetle infestations can be moved to adjacent tree areas which are baited with lures which are attractive to mountain pine beetles.

The invention also pertains to a method of reducing or preventing attack on pine trees by mountain pine beetles by placing verbenone in composition or free form or in controlled release devices on or above the forest floor within the stand of pine trees or by placing verbenone in the forest canopy of the stand of pine trees.

The invention further pertains to a method of preparing a polymer bead containing verbenone by charging a container with plastic beads; sealing the container and heating the container in an oven until the bead temperature is about 60° C.; adding to the preheated beads in the container an amount of verbenone sufficient to enable the beads with absorbed verbenone to reduce attack by mountain pine beetles on pine trees by pouring the verbenone onto the hot beads; sealing the container and turning the container on a horizontal drum mixer in a cabinet heated to a temperature for a time sufficient to allow absorption of the verbenone; removing the loaded container from the mixer and keeping the container in the oven at an elevated temperature for a time sufficient to permit absorption of all verbenone; removing the container from the oven and allowing the container to cool to room temperature over twenty-four hours. The beads can be low density polyethylene, medium density polyethylene, or some other suitable polymer that absorbs verbenone and releases it over a period of time. The polymer can include an ultra violet light absorbant. The verbenone can be added to the preheated beads as aforesaid at concentrations ranging from about 0.01% w/w to about 10.0% w/w, or 0.5% w/w to about 5.0% w/w, or 1.25% w/w to about 3.2% w/w. The beads can be heated to about 60° C. to 80° C. and to about 70° C.

DETAILED DESCRIPTION OF SPECIFIC EMBODIMENTS OF THE INVENTION

Figure 1:
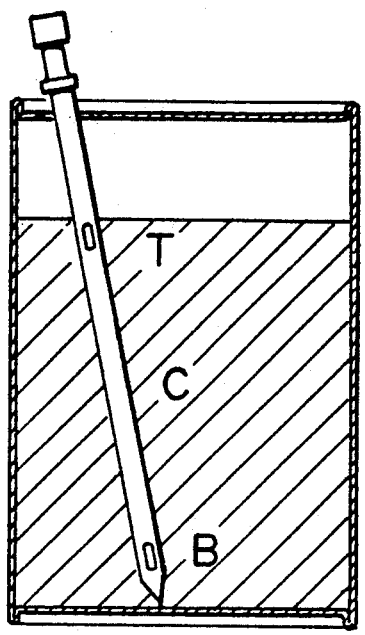
FIG. 1, illustrates a side partial-section view of a drum-bead sampling technique to check quality control.

We have discovered unexpectedly that very small quantities of verbenone (4,6,6-trimethylbicyclo[3.1.1]hept-3-en-2-one) a chemical produced by the mountain pine beetle (Ryker and Yandell, 1983) and from oxidation of a-pinene (4,6,6-trimethylbicyclo[3.1.1]hept-3-ene), a host tree terpene (Borden et al. 1987), will reduce and prevent mountain pine beetle attack on pine trees on which it is placed. Chemical analysis of the verbenone indicated that it consisted of 83% (−)verbenone (negative enantiomer) and 17% (+)-verbenone. We have also discovered that verbenone will reduce and prevent attack on trees near to a tree on which it has been placed. As well, verbenone will reduce and prevent attack on trees in stands in which verbenone has been placed in free form, composition for or in controlled release devices near or on the forest floor or in or near the forest canopy.

The essence of our discovery is the conditions under which verbenone can be usefully applied in a forest to deter mountain pine beetles from attacking living pines in the vicinity of the applied verbenone. We have developed a number of methods and techniques for and managing agencies to implement our invention (1) We have invented a method of repelling the mountain pine beetle from trees by placing verbenone on the trees.

(2) We have devised a method for repelling mountain pine beetle from trees by placing verbenone on some or all of the trees or on or near the ground in composition form or in a controlled release device.

(3) We have invented a method for repelling mountain pine beetle from stands of trees by placing verbenone on or near the tree canopy in controlled release devices.

(4) We have devised a method of repelling mountain pine beetle from stands of trees by placing verbenone on or near the forest floor in controlled release formulations or devices.

Example 1

One experiment (Experiment 1, Table 1) with verbenone was conducted in 1987 near Kelowna, British Columbia, Canada. The objective was to determine if verbenone could prevent containment and concentration of moderate populations of mountain pine beetles in blocks of lodgepole pine trees, *Pinus contorta*, var. *latifolia* Engelmann, where trees had been baited with attractants. In this experiment, ten, 1 ha (100×100 m) blocks were each baited with four mountain pine beetle (MPB) baits each containing myrcene, exo-brevicomin and trans-verbenol as described by Borden et al. (1987). Five of the blocks were treated on a 10×10 m grid with verbenone in devices releasing verbenone (83% (−)-verbenone) at 10 mg per day at 25° C. The beetle population in these blocks was moderate.

TABLE 1

Effect of verbenone deployed prior to attack on numbers of attacks on pine trees per ha by mountain pine beetles in blocks baited with attractive pheromones, June–September, 1987, east of Kelowna, B.C.

|  | Tree Baits deployed at 50 m centers | Verbenone release devices at 10 m centers and tree baits at 50 m centers |
| --- | --- | --- |
| Number of mass attacked trees | 79.4a | 20.4a |
| % Available trees attacked | 13.0a | 5.4b |
| Total attacked trees | 126.8a | 42.2b |
| Attack ratio 1987:1986 | 14.0a | 2.6b |
| % Infested trees not mass attacked | 41.1a | 50.4a |

Note:
Within rows number (means) followed by the same letter are not significantly different by analysis of variance (p = 0.05).

EXAMPLE 2

A second experiment (Experiment 2, Table 2) was conducted in 1987 near Kelowna, British Columbia, Canada in which it was the objective to determine if verbenone could induce mountain pine beetles to disperse from infested lodgepole pine stands. Verbenone (83% (−)-verbenone) was deployed on trees in release devices releasing at 10 mg per day at 25° C. These devices were deployed on a 10×10 m grid in five, 4 ha (200×200 m) blocks. Each device was stapled to the north-facing side of a tree or other suitable object. Five, 4 ha blocks were left as untreated controls. The mountain pine beetle population was high in each block.

TABLE 2

Effect of verbenone deployed prior to attack on numbers of attacks on pine trees per ha by mountain pine beetles, June–September, 1987, east of Kelowna, B.C.

|  | Untreated control blocks | Verbenone release devices deployed at 10 m centers |
| --- | --- | --- |
| Number of mass attacked trees | 100.8a | 25.0b |
| % Available trees attacked | 21.3a | 11.4a |
| Total attacked trees | 141.0a | 53.5a |
| Attack ratio 1987:1986 | 13.2a | 0.2a |
| % Infested trees not mass attacked | 45.7a | 63.2b |

Note:
Within rows numbers (means) followed by the same letter are not significantly different by analysis of variance (p = 0.10).

As can be seen from Table 1, the verbenone substantially decreased mountain pine beetle attacks in stands baited with an attractive bait. This result suggests that verbenone may be effective in preventing mountain pine beetles from attacking new areas despite the presence of successfully attacking beetles, as simulated by the baited trees. As well, Table 2 shows the verbenone effectively decreased mountain pine beetle attacks in stands where it was placed on trees. This result suggests that verbenone can drive beetles out of stands in which further infestation is undesirable.

EXAMPLE 3

A third experiment was conducted in 1987 in Sawtooth Valley in the Sawtooth National Recreational Area, Idaho, U.S.A. Verbenone (83% (−)-verbenone) was deployed in lodgepole pine stands. Treatments in the test were of four types, verbenone, 15 mountain pine beetle baits (trans-verbenol, exo-brevicomin and myrcene), verbenone plus mountain pine beetle lures and untreated control. Each treatment was applied to a 1 ha block and replicated four times. The order of treatment within a replicate was determined randomly and the same order was followed in all replicates to prevent adjacent blocks from having similar treatment. Five MPB baits were used in each block. One bait was placed at the center and one at each cardinal direction from the center approximately 20 m from the outside boundary of the block.

Verbenone-treated blocks had 40 verbenone release devices, each releasing 6–8 mg per day which were placed on trees at approximately 10 m centers. The verbenone bubble caps were stapled to the north sides of trees 2 m above the ground. In blocks which were treated with mountain pine beetle bait plus verbenone, MPB baits and verbenone baits were distributed as described for each alone. Control blocks were untreated.

Treatment effects were based on the percentage of all lodgepole pine of diameters 15.2 cm and larger at 1.3 m above the ground that were infested by mountain pine beetle in 1987. The numbers of trees infested in 1987 were compared to the number of trees infested in 1986 to determine the efficacy of verbenone in deterring attack.

As shown in Table 3, blocks baited with mountain pine beetle bait in 1987 increased attacks by an average of 2577% when compared to these blocks in 1986. Verbenone treated blocks showed an average of 51.4% fewer attacks when compared to the same blocks in 1986. Blocks treated with both the mountain pine beetle bait and the verbenone bubble caps showed an average of only 420.0% increase in attack compared with the same blocks in 1986. Control blocks showed an average of 62.8% more attacks in 1987 compared to the same blocks in 1986.

TABLE 3

Numbers of lodgepole pine killed per ha by mountain pine beetles before and during a test of the efficacy of verbenone to prevent beetle attack, Sawtooth National Forest, Idaho, U.S.A., 1987.

|  | MPB bait attacks/ha | | % Change | VERBENONE, attacks/ha | | % Change | MPB bait + verbenone, attacks/ha | | % Change | Control, attacks/ha | | % Change |
| --- | --- | --- | --- | --- | --- | --- | --- | --- | --- | --- | --- | --- |
| Replicate | 1986 | 1987 | 1986 to 1987 | 1986 | 1987 | 1986 to 1987 | 1986 | 1987 | 1986 to 1987 | 1986 | 1987 | 1986 to 1987 |
| 1 | 6 | 142 | 2266.7 | 0 | 2 | 200.0 | 0 | 16 | 1600.0 | 3 | 0 | −300.0 |
| 2 | 2 | 11 | 450.0 | 14 | 0 | −1400.0 | 2 | 8 | 300.0 | 0 | 0 | 0.0 |
| 3 | 3 | 116 | 3766.7 | 0 | 2 | 200.0 | 14 | 20 | 42.9 | 14 | 0 | −1400.0 |
| 4 | 1 | 52 | 5100.0 | 0 | 3 | 300.0 | 0 | 39 | 3900.0 | 0 | 28 | 2800.0 |
| Average | 3.0 | 80.3 | 2576.7 | 3.5 | 1.8 | −51.4 | 4.0 | 20.8 | 420.0 | 4.3 | 7.0 | 62.8 |

The results in the three experiments (Examples 1–3) show that verbenone, when released from a device attached to trees effectively reduces attack in a stand.

EXAMPLE 4

Another experiment was conducted in 1988 in lodgepole pine stands owned by Plum Creek Inc. located approximately 64 kilometers west of Kalispell, Mont. U.S.A.. One verbenone treatment was applied to 8.1 ha square blocks (284.5 m per side) and replicated five times. The treatment was assigned at random and only blocks that contained 75% lodgepole pine with at least 10% of the stand currently infested were treated. Each block was separated from all other blocks by at least 33.5 m. The treatment consisted of round, plastic beads containing 1.2% verbenone (83% (−)-verbenone) by weight which were applied at the rate of 4.4 kg per ha by dispersing from an aerial seeder carried by a helicopter. The smoothness of the beads ensured some would drop through the canopy and fall to the forest floor. Eight untreated control blocks of 8.1 ha each were selected using the same criteria as for the treatment blocks.

Prior to treatment, each block was surveyed by random start 20.1 m wide transects to obtain estimates of uninfested trees, newly infested trees (1987 attacks) and trees infested prior to 1987. Each tree greater than 12.7 cm in diameter at 1.3 m above ground and falling within a transect swath was assessed. Following application and beetle flight the same transects were reevaluated to measure the diameter at 1.3 m above ground of all newly infested trees. The percent reduction in newly-attacked trees in the treatment blocks from 1987 to 1988 was compared to the percent change in the new attacks from 1987 to 1988 in the control blocks (Table 4).

TABLE 4

Numbers of lodgepole pine attacked per 8.1 ha block by mountain pine beetle before and during a test of the efficacy of aerially applied verbenone to prevent beetle attack, Kalispell, Montana, 1988.

|  | Trees mass attacked per 8.1 ha block | | % Reduction 1987 to 1988 | Relative rates of attack decrease 1987 to 1988 |
| --- | --- | --- | --- | --- |
|  | 1987 | 1988 | | |
| Treatment 1 LPP | 126.5 | 24.0 | 80.5 | 3.5 |
| Control | 203 | 157 | 23.0 | 1.0 |

The results of these tests clearly show that placing verbenone carrier on the forest floor results in a decrease in attack rate of 3.5 times that experienced in the control blocks between 1987 and 1988.

EXAMPLE 5

A fifth experiment was conducted to determine if verbenone is effective in moving mountain pine beetle infestation centers. Four replicates consisting of four plots each were laid out in the Spukunne Creek/Siwash Creek area northeast of Princeton, British Columbia, Canada, 1988. Each plot consisted of three side by side 50×150 m panels. The intention of this design was to simulate a central creek bed, where logging would not be allowed, with flanking loggable areas. Four treatments were applied randomly as follows: 1) Control; no panel treated. 2) Flanking panels baited with 3 mountain pine beetle tree baits each, central panel untreated. 3) Verbenone (83% (−)-verbenone) release devices releasing 10 mg per day at 25° C. deployed in a 10×10 m grid in the central panel (total 75 per panel), flanking panels untreated. 4) Mountain pine beetle tree baits applied as in 2) above in the flanking panels and verbenone release devices deployed as in 3) above in the central panel. Verbenone and baits were applied at the beginning of July well before the first major flight of mountain pine beetles.

The experiment was assessed by 100% cruise of all panels in late September. All attacked trees from the previous year and the new attacks were mapped, and attack densities on the new attacked trees were estimated by counting attacks in two 40×20 centimenters areas taken at opposite sides of the trees at 1.3 m above ground. In order to get an estimate of the number of trees available for attack in each panel the plot boundaries were drawn on 1:15,000 aerial color photographs and trees counted within them.

TABLE 5

Means of percent of available trees which were mass attacked trees (attack density of greater than 31.3 per m²) by panel in experiments assessing the combined use of verbenone and mountain pine beetle tree baits in moving infestations.

|  | Percent of available trees mass attacked | | |
| --- | --- | --- | --- |
| Treatment | Panel 1 | Panel 2 | Panel 3 |
| 1) Untreated | 25.5 | 23 | 22.5 |
| 2) Panels 1 and 3 treated with mountain pine beetle tree baits | 37 | 13.8 | 27 |
| 3) Panel 2 treated with verbenone release devices | 6.5 | 3.5 | 12.5 |
| 4) Panels 1 and 3 treated with mountain pine beetle tree baits; panel 2 treated with verbenone release devices | 22.7 | 8.2 | 20 |

Data were converted to percentages of available trees that were attacked and mass attacked. The results in Table 5 show that placement of mountain pine beetle baits in flanking panels (2) effectively draws infestations into the baited panels. Likewise the placement of verbenone release devices in the central panel displaces infestations into the flanking panels (3). The addition of verbenone release devices to the central panel and mountain pine beetle tree baits to the flanking panels augments the effect of moving infestations from the central panel to the flanking panels (4).

EXAMPLE 6

Verbenone Containing Compositions

A number of verbenone containing compositions were prepared according to the invention. These are discussed in detail below.

Product Name: Mountain Pine Beetle Aerial Repellent—C12 (MTN.P.BTL.AER.REPLINT—C12)

Product Description: MDPE pellets impregnated with Verbenone.

Chemicals: Verbenone (C1-3010/001) with 0.1% antioxidant (AN-330)

Optical Purity: ee=(−)66% (83% (−)-verbenone); chemical purity=97%

Load: 1.2% Verbenone by weight of pellet.

Release Device: MDPE pellet—CIL. 525 (A1-1020/002).

Release Rate: Decreases over time: 0.1 g/kg/day @ 45 day half life, at 24° C.

Expected Life: 70–90 days, depending on field conditions
Suppliers: MDPE, C.I.L. 525 pellet—C.I.L. Edmonton, Alberta, Canada
Verbenone—Bedoukian
Antioxidant—Ethyl Corporation
Storaqe Information: Store loaded pellets in air-tight, galvanized steel drum.

EXAMPLE 7

Product Name: Mountain Pine Beetle Aerial Repellent—E30 (MTN.P.BTL.AER.REPLLNT—E30)
Product Description: Polymer pellets impregnated with Verbenone.
Chemicals: Verbenone (C1-3010/001) with 0.1% antioxidant (AN-330)
Optical Purity:ee=(—)66% (83% (—)-verbenone); chemical purity =97%
Load: 3.0% Verbenone by weight of pellet.
Release Device: PTI pellet—E/1989 (A1-1020/007).
Release Rate: Not determined
Expected Life: 70–90 days, depending on field conditions
Suppliers:
Verbenone—Bedoukian
Antioxidant—Ethyl Corporation
Storage Information: Store loaded pellets in air-tight, galvanized steel drum.

EXAMPLE 8

Verbenone beads (pellets) were prepared according to the following Verbenone ARD Bead Loading Process:
1. A standard 45 gallon steel drum is charged with about 80 kg of plastic beads.
2. The drum is sealed and heated in an oven until the bead temperature is 60° C.
3. To the preheated beads in the drum is added the appropriate amount of verbenone; 1.25% (w/w) for C-12 and 3.2% (w/w) for E-30 by pouring the neat material onto the hot beads.
4. The drum is sealed and turned on a horizontal drum mixer in a cabinet heated to a temperature for a time sufficient to allow absorption of all verbenone.
5. The loaded drum is removed from the mixer and kept in the oven at an elevated temperature for a time sufficient absorption of all verbenone.
6. The drum is removed from the oven and allowed to cool to room temperature over twenty-four hours. The controlled release devices are then sampled and packaged.

QUALITY CONTROL FOR VERBENONE A.R.D.

Procedure for Collecting Verbenone Controlled Release Device Sample

1. From the first completed verbenone loaded controlled release device drum, collect samples from the top (T), center (C) and bottom (B) of the drum. (See FIG. 1).
2. This is accomplished by inserting a grain sampler probe through the bung diagonally. (See FIG. 1).
3. A twist of the grain sampler probe encases the three individual verbenone controlled release device samples.
4. All samples are clearly marked with the date of collection, drum batch number and sample location.
5. The samples are analysed by a quality control technician for verbenone content.

EXAMPLE 9

A controlled verbenone release apparatus was made as follows:
Product Name: Verbenone Bubble Cap
Product Description: A single component bubble cap
Chemicals: Verbenone (C1-3010/001) with 0.1% antioxidant (AN-330)
Optical Purity: ee=(—)66% (83% (—)-verbenone); chemical purity=97%
Load: WEIGHT—0.78 g VOLUME—0.80 ml
Release Device:10 mil back LDPE (A2-1013/010) bubble; 40 u translucent LDPE (A2-1010/021) membrane
Release Rate: 10 mg/day @ 24° C.
Expected Life: 75+ days
UV-protection: Yes
Suppliers:
Verbenone—Bedoukian
Antioxidant 330—Ethyl Corporation
10 mil LDPE—False Creek Industries
40 u LDPE—General Paint
Storage Information: Below 0° C. in mylar bag.

The Complete Bubble Cap

Figure 2:
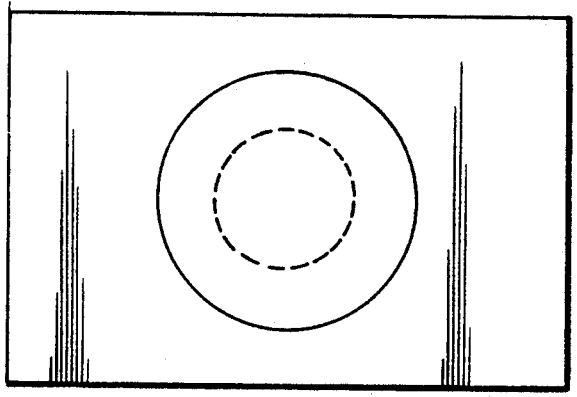
FIGS. 2 and 3 illustrate respectively plan and side views of the construction of a bubble cap containing verbenone.
Figure 3:
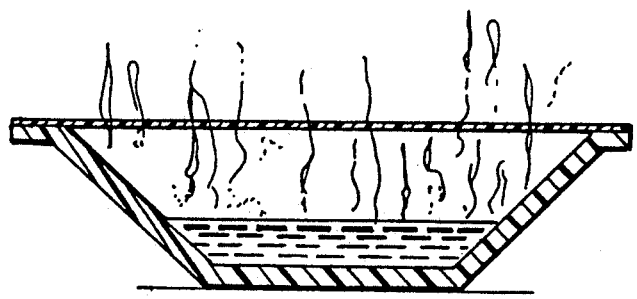

Circular cavities or bubbles are created by a combined heat and vacuum system in 10 mm thick low density polyethylene film strips (2" in width). Each cavity has dimensions as described in FIGS. 2 and 3.

Once formed 0.80 ml (0.78g) 0.01 g of active ingredient verbenone is dispensed into each cavity using a repeat pipette dispenser. Dispensing is caused by physical pressure on the pipette plunger provided by a manual or hydraulic system.

Once the active ingredient has been dispensed into the respective cavity a 20 micron thick low density polyethylene film strip is sealed onto the film strip containing the cavity via a impulse heat sealer. This forms the release device.

The combined strips containing the active ingredients are cut between cavities to produce the final verbenone bubble cap.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

Amman, G. D., R. W. Thier, M. D. McGregor and R. F. Schmitz. 1989. Efficacy of verbenone in reducing lodgepole pine infestation by mountain pine beetles in Idaho. Can. J. For. Res. 19: 60–64.

Borden, J. H., J. E. Conn, L. M. Friskie, A. C. Oehlschlager, H. D. Pierce, Jr. and B. E. Scott. 1983. Semiochemicals for the mountain pine beetle, *Dendroctonus ponderosae*, in British Columbia: field trapping studies. Can. J. For. Res. 13: 320–324.

Borden, J. H., and B. S. Lindgren. 1988. The role of semiochemicals in IPM of the mountain pine beetle, pp. 247-25 In T. L. Payne and H. Saarenma [Eds.], Integrated Control of Scolytid Bark Beetles, Virginia Polytechnic Institute and State University, Blacksburg, Va., December 1988, 356 pp.

Borden, J. H., L. J. Chong, J. E. Conn, L. M. Friskie, H. D. Pierce, Jr., A. C. Oehlschlager and B. E. Scott. 1987. Semiochemicals for the mountain pine beetle, *Dendroctonus ponderosae* in British Columbia: baited tree studies. Can. J. For. Res., 13, 325–333.

Borden, J. H., L. J. Chong, J. E. Conn, H. D. Pierce, Jr. and A. C. Oehlschlager. 1986. Canadian Patent 1,212,044, Composition for Attracting and Methods of Combating Mountain Pine Beetles.

Borden, J. H., L. J. Chong, B. D. Johnston, H. D. Pierce, Jr., A. C. Oehlschlager and L. C. Ryker. 1987. Response of the mountain pine beetle, *Dendroctonus ponderosae* Hopkins (Coleoptera: Scolytidae), to five semiochemicals in British Columbia lodgepole pine forests. Can. J. For. Res. 17, 118–128.

Borden, J. H., J. R. Handley, J. A. McLean, R. M. Silverstein, L. Chong, K. N. Slessor, B. D. Johnston and H. R. Schuler. 1980. Enantiomer-based specificity in pheromone communication by two sympatric Gnathotrichus species (Coleoptera: Scolytidae) J. Chem. Ecol. 6: 445–456.

Chatelain, M. P. and J. A. Schenk. 1984. Evaluation of frontalin and exo-brevicomin as kairomones to control the mountain pine beetle in lodgepole pine. Environ, Entomol. 13: 1666–1674.

Furniss, M. M., R. W. Clausen, G. P. Markin, M. D. McGregor, and R. L. Livingston. 1981. Effectiveness of Douglas-fir anti-aggregative pheromone applied by helicopter. USDA For. Serv. Gen. Techn. Rep. INT-101, 6 pp., Intermountain For. and Range Exp. Stn., Ogden, Utah.

Furniss, M. M., G. P. Markin and V. J. Hager. 1982. Aerial application of Douglas-fir beetle anti-aggregative pheromone: Equipment and evaluation. USDA For. Serv. Gen. Techn. Rep. INT-137, 9 pp., Intermountain For. and Range Exp. Stn., Ogden, Utah.

Lanier, G. N. and D. L. Wood. 1975. Specificity of response to pheromones in the genus Ips (Coleoptera: Scolytidae). J. Chem. Ecol. 1: 9–23.

Libbey, L. M., L. C. Ryker and K. L. Yandell. 1985. Laboratory and field studies of volatile released by *Dendroctonus ponderosae* Hopkins (Coleoptera: Scolytidae). Z. Angew. Entomol. 100: 38–392.

Lindgren, B. S, J. H. Borden, G. H. Cushion, L. J. Chong and C. J. Higgins. 1989. Reduction of mountain pine beetle attacks by verbenone in lodgepole pine stands in British Columbia. Can. J. For. Res. 19:65–68.

Lindgren, B. S., M. D. McGregor, R. D. Oakes, and H. E. Meyer. 1988. Effect of MCH and baited Lindgren traps on Douglas-fir beetle attacks on felled trees. Z. ang. Ent. 105:289–294.

Lindgren, B. S., M. D. McGregor, R. D. Oakes, and H. E. Meyer. 1989. Suppression of spruce beetle attacks by MCH released from bubble caps. Western J. Appl. For. 4: 49–52.

Pitman, G. B., J. P. Vité, G. W. Kinzer and A. F. Fentiman, Jr. 1968. Bark beetle attractants: trans-verbenol isolated from Dendroctonus. Nature (London). 218: 168–169.

Pitman, G. B. 1971. Trans-verbenol and alpha-pinene: their utility in manipulation of the mountain pine beetle. J. Ecol. Entomol. 64; 426–430.

Rudinsky, J. A., M. E. Morgan, L. M. Libbey and T. B. Putnam. 1974a. Antiaggregative-rivalry pheromone of the mountain pine beetle, and a new arrestant of the southern pine beetle. Environ. Entomol. 3: 90–98.

Rudinsky, J. A., C. Sartwell, Jr., T. M. Graves, and M. E. Morgan. 1974b. Granular formulation of methylcyclohexenone: an anti-aggregative pheromone of the Douglas-fir and spruce bark beetles. Z. ang. Ent. 75:254–263.

Ryker, L. C. and J. A. Rudinsky. 1982. Field bioassay of exo and endo-brevicomin as antiaggregation pheromones for *Dendroctonus ponderosae* in lodgepole pine. J. Chem. Ecol. 8:707–707.

Ryker, L. C. and K. L. Yandell. 1983. Effect of verbenone on aggregation of *Dendroctonus ponderosae* Hopkins (Coleoptera: Scolytidae) to synthetic attractant. Z. Angew. Entomol. 96: 452–459).

We claim:

1. A method of reducing the incidence of attack of mountain pine beetle, *Dendroctonus ponderosae*, on a stand of trees which has therein at least some trees of the species *Pinus contorta* and which are susceptible to attach by said mountain pine beetle, comprising dispensing in said stand of trees a mountain pine beetle inhibiting effective amount of a composition having an active ingredient consisting of verbenone with about 83% of the (−) enantiomer, and wherein the composition is dispersed in the stand of trees in amounts such that the amount of the active ingredient is about 240 to 1,000 mg. average per day per hectare.

2. A method according to claim 1 wherein the verbenone is dispersed in release devices which are placed on some of the trees in the stand of trees.

3. a method according to claim 2 wherein the verbenone is dispersed in a bubble cap release device.

4. A method according to claim 2 wherein the verbenone is dispersed in a controlled release agent.

5. A method according to claim 4 wherein the controlled release agent is a polymer bead containing the verbenone.

6. A method according to claim 1 wherein the verbenone is dispersed in release devices which are placed in a canopy of the stand of trees.

7. A method according to claim 1 wherein the verbenone is dispersed in release device which are placed on or above a forest floor within the stand of trees.

8. A method according to claim 1 wherein the verbenone is dispersed in release devices which are placed on or approximate to at least some of the trees in the stand of trees.

9. A method according to claim 1 wherein the verbenone is at least placed on said trees which are infected by said mountain pine beetle.

10. A method according to claim 1 wherein trees near or adjacent said stand of trees are baited with lures which attract said mountain pine beetle.

11. A method according to claim 1 wherein the verbenone is broadcast over said stand of trees from an aircraft.

* * * * *